(12) United States Patent
Park et al.

(10) Patent No.: US 12,099,060 B2
(45) Date of Patent: Sep. 24, 2024

(54) NANOVESICLE COMPRISING HETERODIMERIC G-PROTEIN COUPLED RECEPTOR, METHOD FOR PREPARING NANOVESICLE, FIELD EFFECT TRANSISTOR-BASED TASTE SENSOR COMPRISING NANOVESICLE, AND METHOD FOR MANUFACTURING TASTE SENSOR

(71) Applicant: Seoul National University R&DB Foundation, Seoul (KR)

(72) Inventors: Tai Hyun Park, Seoul (KR); Seung Hun Hong, Seoul (KR); Hyun Seok Song, Gyeonggi-do (KR); Hye Jun Jin, Seoul (KR); Sae Ryun Ahn, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 1120 days.

(21) Appl. No.: 16/839,623

(22) Filed: Apr. 3, 2020

(65) Prior Publication Data

US 2020/0271644 A1 Aug. 27, 2020

Related U.S. Application Data

(62) Division of application No. 15/022,298, filed as application No. PCT/KR2013/008376 on Sep. 16, 2013, now Pat. No. 10,914,736.

(30) Foreign Application Priority Data

Sep. 16, 2013 (KR) .................. 10-2013-0111033

(51) Int. Cl.
  *G01N 21/64* (2006.01)
  *B01F 23/00* (2022.01)
  (Continued)

(52) U.S. Cl.
  CPC ....... *G01N 33/5438* (2013.01); *C07K 14/705* (2013.01); *G01N 27/4145* (2013.01);
  (Continued)

(58) Field of Classification Search
  CPC .......... G01N 33/5438; G01N 27/4145; G01N 33/5308; G01N 33/54373; G01N 33/74;
  (Continued)

(56) References Cited

U.S. PATENT DOCUMENTS

2004/0191862 A1* 9/2004 Zoller ............... G01N 33/5041
                                                                435/325
2004/0241765 A1   12/2004 Zweig
                                (Continued)

FOREIGN PATENT DOCUMENTS

KR       20090121909 A  * 11/2009  ............ H10K 10/23
KR    10-2011-0117695 A    10/2011
                                (Continued)

OTHER PUBLICATIONS

Feng, Xue, et al. "Detection of low concentration oxygen containing functional groups on activated carbon fiber surfaces through fluorescent labeling." Carbon 44.7 (2006): 1203-1209. (Year: 2006).*
(Continued)

*Primary Examiner* — Jennifer Wecker
*Assistant Examiner* — Oyeleye Alexander Alabi
(74) *Attorney, Agent, or Firm* — Honigman LLP

(57) ABSTRACT

The present invention relates to a nanovesicle comprising a heterodimeric G-protein coupled receptor, a method for preparing the nanovesicle, a field effect transistor-based taste sensor comprising the nanovesicle, and a method for manufacturing the taste sensor. The field effect transistor based taste sensor functionalized by the nanovesicle comprising the heterodimer G-protein coupled receptor according to the present invention has excellent sensitivity and selectivity
(Continued)

and may highly specifically detect a sweet taste substance in real time, by using the heterodimeric G-protein coupled receptor and the nanovesicle comprising the same.

19 Claims, 4 Drawing Sheets

(51) Int. Cl.

| | |
|---|---|
| *B01F 23/41* | (2022.01) |
| *B01F 101/23* | (2022.01) |
| *B23Q 17/24* | (2006.01) |
| *C07K 14/705* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 27/414* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *H10K 10/46* | (2023.01) |
| *H10K 85/00* | (2023.01) |
| *H10K 85/20* | (2023.01) |

(52) U.S. Cl.
CPC ... *G01N 33/5308* (2013.01); *G01N 33/54373* (2013.01); *G01N 33/74* (2013.01); *H10K 10/46* (2023.02); *H10K 85/761* (2023.02); *G01N 2333/705* (2013.01); *G01N 2333/726* (2013.01); *G01N 2400/00* (2013.01); *H10K 85/225* (2023.02)

(58) Field of Classification Search
CPC ....... G01N 2333/705; G01N 2333/726; G01N 2400/00; G01N 33/68; C07K 14/705; H10K 10/46; H10K 85/761; H10K 85/225; C12N 15/85; C12P 21/02

See application file for complete search history.

(56) References Cited

U.S. PATENT DOCUMENTS

2009/0155816 A1* 6/2009 Hong ................. G01N 27/3278
  435/7.8
2012/0231969 A1 9/2012 He et al.

FOREIGN PATENT DOCUMENTS

| KR | 20110108661 A * | 10/2011 | ......... G01N 27/4146 |
| KR | 10-2012-0083987 A | 7/2012 | |
| KR | 10-2013-0008216 A | 1/2013 | |
| KR | 10-1684620 B1 | 12/2016 | |
| WO | WO-2006103872 A1 * | 10/2006 | ............. B82Y 10/00 |

OTHER PUBLICATIONS

Bezanilla, Francisco. "Voltage-gated ion channels." Biological Membrane Ion Channels: Dynamics, Structure, and Applications (2007): 81-118. (Year: 2007).*
International Search Report dated Jun. 13, 2014 from International Application No. PCT/KR2013/008376.
Written Opinion dated Jun. 13, 2014 from International Application No. PCT/KR2013/008376.
International Preliminary Report on Patentability dated Mar. 22, 2016 from International Application No. PCT/KR2013/008376.
Song et al., "Fabrication of FET-Type of Sweet Taste Biosensor Functionalized with Nanovesicles Containing Human Sweet Taste Receptor," IBS 2012 15th International Biotechnology Symposium and Exhibition, Sep. 16-21, 2012, EXCO, Daegu, Republic or Korea.
Jung, "Development of Dopamine Biosensor Based on Human Dopamine Receptor-Containing Nonovesicle and PEDOT Nanotube," English language translation of Master's Thesis, Seoul National University, Chemical and Biological Engineering, Feb. 2013, pp. 23, 24, and 32-36.
Assadi-Porter et al., "Interactions Between the Human Sweet-Sensing T1R2-T1R3 Receptor and Sweeteners Detected by Saturation Transfer Difference NMR Spectroscopy," Biochimica et Biophysica Acta, vol. 1798, No. 2, 2010, pp. 1-12.
Wang et al., "A Novel Sweet Taste Cell-Based Sensor," Biosensors and Bioelectronics, vol. 26, No. 2, 2010, pp. 929-934.

* cited by examiner

PSE Functionalization

Nanovesicle Immobilization

FIG. 2A
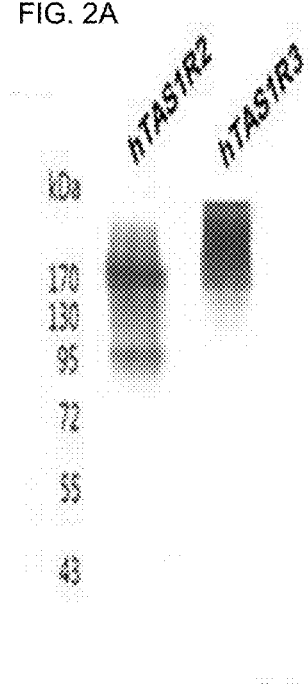
FIG. 2B
FIG. 2C
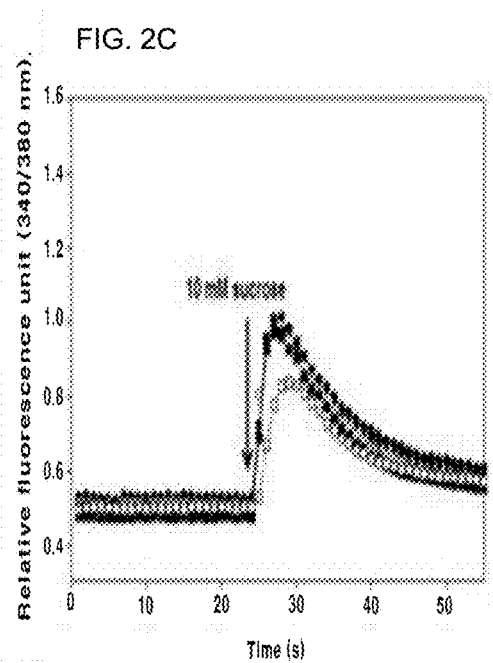
FIG. 2D
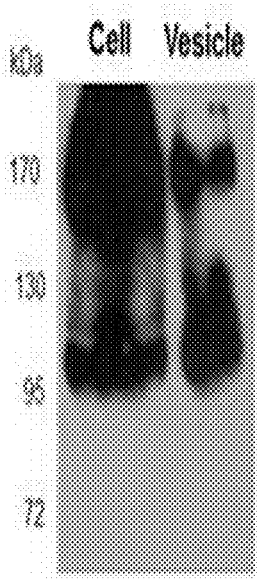
FIG. 2E
FIG. 2F
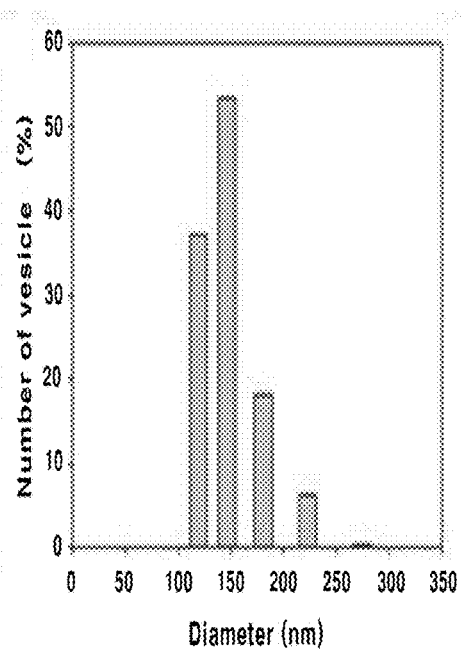

FIG. 4A
FIG. 4B
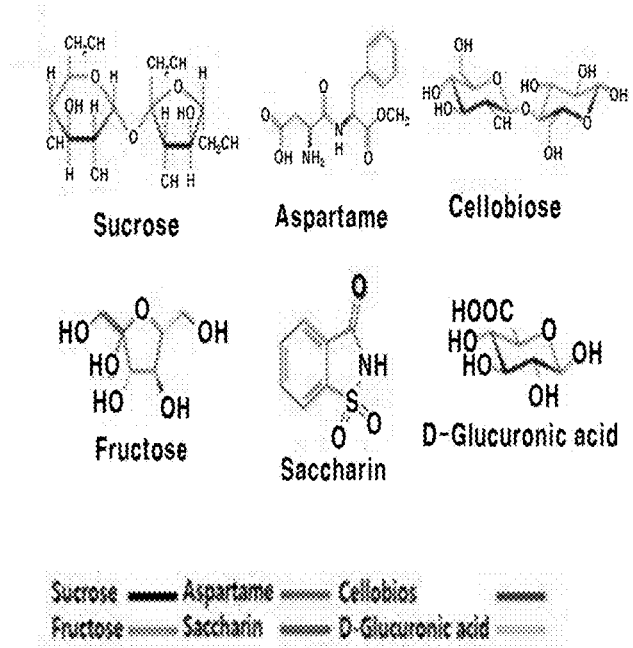
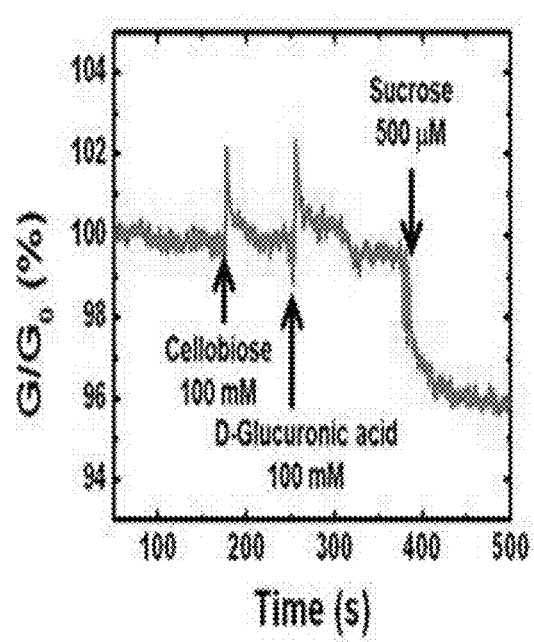
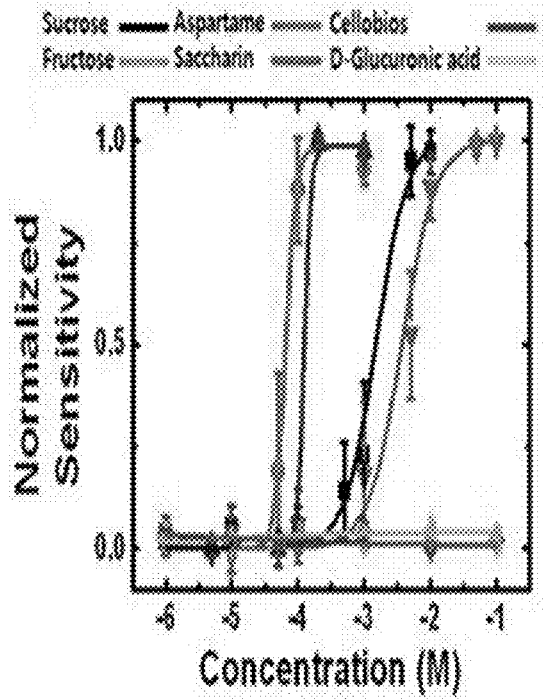
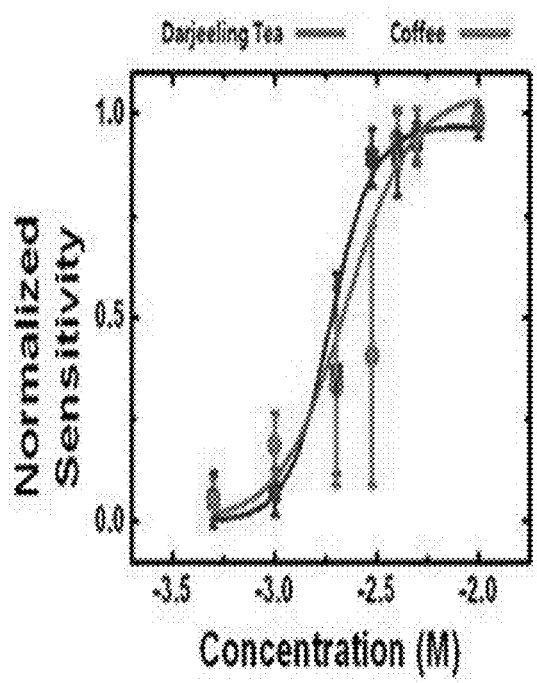
FIG. 4C
FIG. 4D

NANOVESICLE COMPRISING HETERODIMERIC G-PROTEIN COUPLED RECEPTOR, METHOD FOR PREPARING NANOVESICLE, FIELD EFFECT TRANSISTOR-BASED TASTE SENSOR COMPRISING NANOVESICLE, AND METHOD FOR MANUFACTURING TASTE SENSOR

CROSS-REFERENCE TO RELATED APPLICATIONS

This application is a divisional of U.S. patent application Ser. No. 15/022,298, filed Mar. 16, 2016, which is a U.S. national phase of PCT International Patent Application No. PCT/KR2013/008376, filed Sep. 16, 2013, which claims priority to Korean Patent Application No. 10-2013-0111033, filed Sep. 16, 2013, the contents of each of which are incorporated herein by reference in their entirety.

BACKGROUND OF THE INVENTION

Field of the Invention

This document relates to a nanovesicle comprising a heterodimer G-protein coupled receptor, a method for preparing the nanovesicle, a field effect transistor-based taste sensor comprising the nanovesicle, and a method for manufacturing the taste sensor.

Discussion of the Related Art

Human various sensing systems may perceive many stimuli and detect magnitudes thereof. Specifically, in a human visual sensing system, an opsin acts as a receptor to receive a light signal to be transferred to a visual neuron (Fesenko, E. E. et al., Nature, 310-313(1985); Nathans, J. et al., Cell, 807-814(1983); Berridge, M. J. et al., Nature, 315-321(1984); Nathans, J. et al., Science, 193-202(1986)). It has been found out recently that, in a human olfactory sensing system, there is an olfactory receptor reacting with an odorant molecule on a villus surface (Buck, L. et al., Cell, 175-187(1991)). Characteristics of the receptors of such visual and olfactory sensing systems receptor are that each of the receptors has seven transmembrane domain motifs and is bound to a GTP-binding protein (G protein). The G protein is a heterotrimeric GTP-binding protein to couple the receptor and an effector to each other during many signals transfers (Shapiro, R. A. et al., J. Biol. Chem., 18397-18403 (1988); Dixon, R. A. F. et al., EMBO J., 3269-3275 (1987); Karnik, S. S. et al., Proc. Natl. Acad. Sci. U.S.A., 8459-8463(1988); Karnik, S. S. et al., J. Biol. Chem., 17520-17524 (1990)).

A suggestion has been generally appreciated that the visual and olfactory signal transfers are triggered via activations of the G protein coupled proteins. However, molecular biological studies for taste receptors have been smaller than those for the visual and olfactory receptors. It has been discovered based on the molecular biological studies for the taste receptors that a signal stimulated by tastant molecules is originated from taste pores in surfaces of taste cells in a fungiform papillae, a foliate papillae and a circumvallate papillae of a tongue. In the taste pores, several taste ligands performs depolarization or hyperpolarization for the taste cells so as to adjust emission of neurotransmitters from the taste cells. In this connection, adjacent taste cells are inter-associated to adjust the signal to be transferred to a centripetal gustatory nerve. A taste receptor protein for a sweet taste, etc. is one kind of the G protein coupled receptors (GPCRs), and passes through seven membranes. The taste receptor protein may reside at a surface of and/or within a lipid bilayer.

The taste is classified into salty, sour, sweet, and bitter tastes depending on stimulating substance. Molecular mechanisms for transferring the four tastes have been partially discovered. Regarding the salty taste, for transferring the taste, Na ions flow through Na channels; regarding the sour taste, for transferring the taste, H ions are blocked from flowing through K, and Na channels; and regarding the bitter taste and sweet taste, the transferring of the tastes is based on a guanine nucleotide binding protein (G protein) dependent mechanism (Kinnamon, S. C., Trends Neurosci, 491-496(1988); Avenet, P. et al., J. Membrane Biol., 1-8(1989); Roper, S. D., Ann. Rev. Neurosci., 329-353(1989)).

It has been discovered that regarding the bitter taste, a bitter taste compound induces emission of $Ca^{2+}$ ions from a storage thereof as a G-bound receptor, where the G-protein may be involved.

Regarding the sweet taste, a sweet taste compound generates a cyclic AMP (cAMP) in a tongue membrane on a GTP-dependent manner (Striem, B. J. et al., Biochem, J., 121-126(1989): Striem, B. J. et al., Chem. Senses, 529-536 (1990)). When the cAMP is microinjected into a taste cell, the cAMP not only inactivates but also depolarizes $K^+$ channels (Gubler, U, et al., Gene (Amst.), 263-269(1983); Hanahan, D., J. Mol. Biol., 557-580(1983); Hattori, M. et al., Anal. Biochem., 232-238(1986)), and an adenylyl cyclase and a cAMP-PDE (phosphodiesterase) are found out in the taste tissue at a high concentration. This may imply that activation of the sweet taste receptor increases a level of the cAMP via a transduction pathway to depolarize the taste cell in connection to the taste G protein.

Korean Patent Number 10-1684620 discloses a taste sensing device having a lipid molecule membrane as a taste sensor and outputting an electrical signal indicating taste information. Further, the Korean Patent Number 10-1684620 further discloses a single wall CNT (carbon nanotube) FET (field effect transistor) including a hTAS2R based bitter taste receptor protein.

However, the above patent document discloses only a single G protein as the taste receptor protein. In other words, a prior art including the above patent document does not disclose a taste sensor including a heterodimeric G-protein coupled receptor (GRPC).

SUMMARY OF THE INVENTION

With consideration of the above, the present invention is aimed to provide a nanovesicle including a heterodimeric G protein coupled receptor as a sweet taste receptor protein, and a method for manufacturing the nanovesicle.

The present invention is further aimed to provide a field effect transistor based taste sensor including the nanovesicle and a method for manufacturing the field effect transistor based taste sensor.

In order to solve the above challenges, the present invention provides a method for manufacturing a nanovesicle including a heterodimeric G protein coupled receptor, the method comprising:

a) transforming an animal cell into a gene coding a heterodimeric G protein coupled receptor;

b) applying a compound treatment to the animal cell such that the animal cell secretes a nanovesicle including a taste receptor protein; and c) separating the secreted nanovesicle from the animal cell.

The method for manufacturing the nanovesicle including the heterodimeric G protein coupled receptor in accordance with the present invention is shown in FIGS. 1A and 1B.

In the taste sensor in accordance with the present invention, the heterodimeric G protein coupled receptor may include two genes selected from a group consisting of hTAS1R1, hTAS1R2 and hTAS1R3. A TAS1R taste receptor group known as coding the sweet taste and savory taste receptor may include total three genes: TAS1R1, TAS1R2, and TAS1R3. Typically, the genes may be in a form of a heterodimer to code the receptor for each taste. To be specific, a heterodimer of the TAS1R1 gene and TAS1R3 gene may act as the savory taste receptor, while a heterodimer of the TAS1R2 gene and TAS1R3 gene may act as the sweet taste receptor.

In one embodiment of the present invention, the heterodimeric G protein coupled receptor may include a combination of hTAS1R2 and hTAS1R3. In one embodiment of the present invention, the heterodimeric G protein coupled receptor including the hTAS1R2 and hTAS1R3 may include a signal system such as a G protein, adenyl cyclase, and ion channels. In one embodiment of the present invention, the heterodimeric G protein coupled receptor may improve a cAMP level via signal transfer in the cell resulting from binding between the sweet taste substance and the sweet taste receptor. This may lead to accumulation of $Ca^{2+}$ in the nanovesicle and thus an improved concentration of $Ca^{2+}$ therein.

In the method for manufacturing the nanovesicle in accordance with the present invention, the a) step may comprise adding a compound including an ester group. For example, the compound including the ester group may include Fura 2-acetoxymethyl. In this connection, in the cell, there may be a non-specific esterase, which may perform hydrolysis for the AM ester group to change the cell to a form sensitive to the $Ca^{2+}$.

In the method for manufacturing the nanovesicle in accordance with the present invention, the compound in the b) step may include cytochalasin B.

In the method for manufacturing the nanovesicle in accordance with the present invention, the animal cell at the a) step may include a human embryonic kidney-293 (HEK-293) cell line expressing a sweet taste substance receptor protein.

Further, the present invention provides a nanovesicle including a heterodimeric G protein coupled receptor manufactured by the method for manufacturing the nanovesicle in accordance with the present invention.

In the present invention, it may be preferable that the nanovesicle has a size of 100 nm to 250 nm. When the nanovesicle has the above ranged size, the nanovesicle may be sufficiently absorbed onto a nanostructure, thereby to sufficiently secure a region for detecting a sweet taste substance.

The nanovesicle in accordance with the present invention has a size much smaller than a size of the cell, but has an intra-cell signal transfer function as the cell has. The nanovesicle in accordance with the present invention is more easy to be maintained than the cell, and is more suitable for manufacturing a nano-device. The nanovesicle with a size of 100 nm to 250 nm is immobilized onto a substrate, and, thereafter, amide binding between a carbon nanotube and the nanovesicle. In this connection, a size of the nanovesicle immobilized during the amide binding is smaller than a size of the nanovesicle manufactured by the manufacturing method.

Further, the present invention provides a field effect transistor based taste sensor comprising:
  a substrate;
  source and drain electrodes formed on the substrate, wherein the source and drain electrodes are spaced from each other;
  a nanostructure formed on the substrate and between the source and drain electrodes, wherein the nanostructure electrically contacts the source and drain electrodes, and modifies a surface of the substrate; and
  the nanovesicle including the heterodimeric G protein coupled receptor in accordance with the present invention, wherein the nanovesicle is immobilized onto the nanostructure.

A structure of the field effect transistor based taste sensor in accordance with the present invention is schematically shown in FIG. 3A.

Further, the present invention provides a method for manufacturing the field effect transistor based taste sensor, the method comprising:
  a) providing a substrate;
  b) forming a nanostructure on a surface of the substrate;
  c) forming source and drain electrodes on the substrate, wherein the source and drain electrodes are spaced from each other, and electrically contact the nanostructure; and
  d) immobilizing a nanovesicle including a heterodimeric G protein coupled receptor onto a surface of the nanostructure.

The method for manufacturing the field effect transistor based taste sensor in accordance with the present invention may further comprise modifying the substrate surface to have an amine group therein.

In the above method, modifying the substrate surface to have the amine group therein may include a treatment using an amine group containing silane coupling agent selected a group consisting of 3-aminopropylmethyl dimethoxy silane, 3-(2-aminoethyl)aminopropyltrimethoxy silane, 3(2-aminoethyl)aminopropylmethyldimethoxy silane, 3-amino-propyltrimethoxysilane, N-phenyl-3-aminopropyltrimethoxy silane, 3-aminopropylmethyldiethoxy silane, and 3-aminopropyltriethoxy silane.

The method for manufacturing the field effect transistor based taste sensor in accordance with the present invention may further comprise modifying the nanostructure surface to have therein a substance including a pyrene and amine group. The substance including the pyrene and amine group may include at least one selected from a group consisting of pyrene methylamine, 1-aminopyrene, and pyrenebutyric succinimide ester (PSE).

In the method for manufacturing the field effect transistor based taste sensor in accordance with the present invention, the nanostructure may be formed on the substrate by immersing the surface modified substrate in a nanostructure containing solution or exposing the surface modified substrate to a nanostructure containing gas.

In the method for manufacturing the field effect transistor based taste sensor in accordance with the present invention, the nanostructure may include a nanotube, nanowire, nanorod, nanoribbon, nanofilm, or nanoball.

In the method for manufacturing the field effect transistor based taste sensor in accordance with the present invention, the nanovesicle including the heterodimeric G protein coupled receptor in accordance with the present invention may be immobilized onto the surface modified nanostructure surface. The immobilization of the nanovesicle including the heterodimeric G protein coupled receptor onto the surface modified nanostructure surface may include spreading and drying a solution containing the nanovesicle including the heterodimeric G protein coupled receptor on the surface modified nanostructure surface to immobilize the sweet taste receptor protein.

Further, the present invention provides a sweet taste substance detection method comprising: exposing a sweet taste substance to the taste sensor in accordance with the present invention; and measuring conductance variation resulting from binding between the sweet taste receptor protein and sweet taste substance when the sweet taste substance containing solution or sweet taste substance containing gas contacts with the taste sensor. In one embodiment of the present invention, the sweet taste substance may be detected by contacting the sweet taste substance containing solution or sweet taste substance containing gas with the field effect transistor based taste sensor.

In the field effect transistor based taste sensor of the present invention, the sweet taste substance is bound to the G protein coupled receptor including the human taste receptor hTAS1R2 and hTAS1R3, such that positive ions flow into the nanovesicle via the cAMP path to cause the conductance variation.

Using the taste sensor of the present invention, a variety of sweeteners including a natural sugar (sucrose, fructose, glucose, maltose, lactose), a sweet taste amino acid (D-tryptophane), and an artificial sweetener (aspartame, saccharin, acesulfame K, cyclamate, sucralose) may be detected.

Effect of the Invention

The field effect transistor and taste sensor functionalized by the nanovesicle including the heterodimeric G protein coupled receptor in accordance with the present invention may detect the sweet taste substance using the G protein coupled receptor in a real time manner and with an excellent sensitivity and selectivity and at a high specific degree up to a µM range.

BRIEF DESCRIPTION OF DRAWINGS

FIG. 2A shows a measurement result of whether a G protein coupled receptor is expressed or not for a transformed cell and nanovesicle including a heterodimeric G protein coupled receptor, using a western blot analysis method, in accordance with one embodiment of the present invention.

FIG. 2B shows a measurement result of whether a G protein coupled receptor is expressed or not for a transformed cell and nanovesicle including a heterodimeric G protein coupled receptor, using a fluorescence image of a confocal fluorescence microscope, in accordance with one embodiment of the present invention.

FIG. 2C illustrates a reaction magnitude of a transformed cell including a heterodimeric G protein coupled receptor with a sucrose, in accordance with one embodiment of the present invention.

FIG. 2D shows a measurement result of whether a heterodimeric G protein coupled receptor is expressed or not for a transformed cell and nanovesicle including a heterodimeric G protein coupled receptor, using a western blot analysis method, in accordance with one embodiment of the present invention.

FIG. 2E illustrates a measurement size distribution of a nanovesicle including a heterodimeric G protein coupled receptor using a DLS analysis method in accordance with one embodiment of the present invention.

FIG. 2F illustrates a reaction magnitude of a nanovesicle with a sucrose, where the nanovesicle including a heterodimeric G protein coupled receptor is manufactured in accordance with one embodiment of the present invention.

FIG. 4A shows chemical structures of various sweeteners.

FIG. 4B shows a real-time response showing the human tongue-like selectivity of a field effect transistor based on a nanovesicle.

FIG. 4C shows a dose-dependent response of a field effect transistor based on a nanovesicle to various sweet sugars (natural sweeteners), artificial sweeteners, and tasteless sugars.

FIG. 4D shows dose-dependent responses of a field effect transistor based on a nanovesicle to sucrose inDBPS, Darjeeling tea, and coffee.

DETAILED DESCRIPTION OF THE INVENTION

Figure 1A:
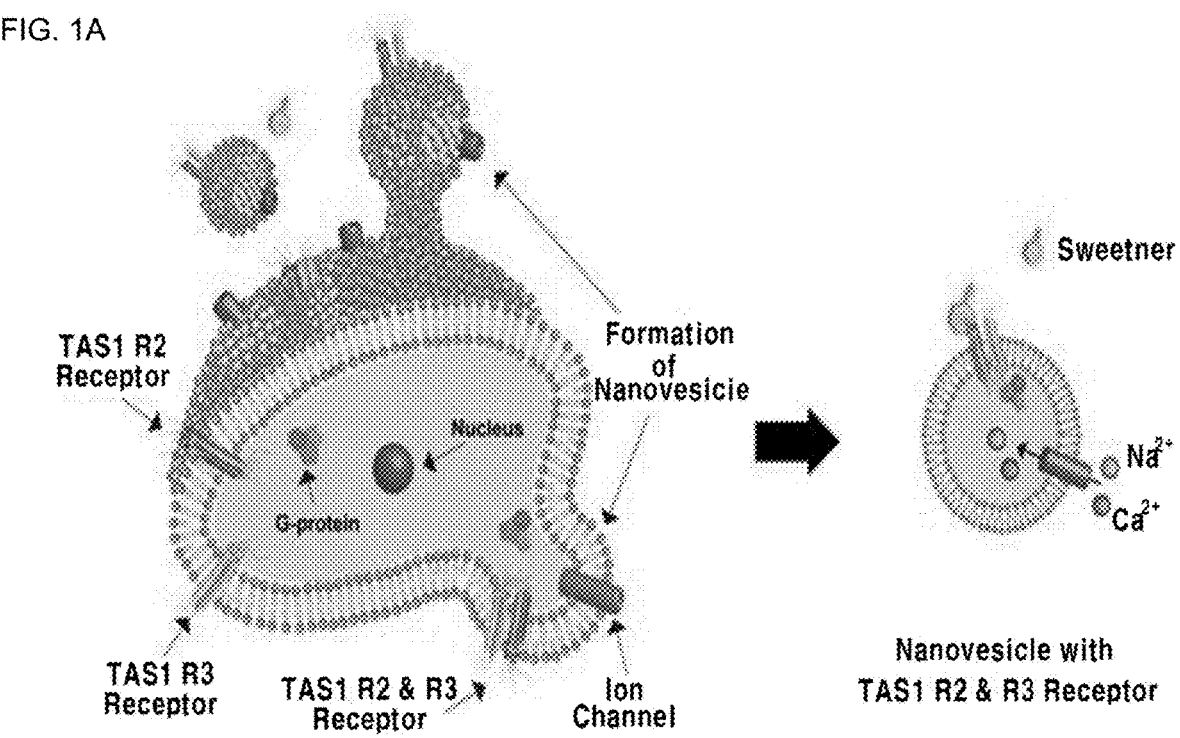
FIG. 1A illustrates a method for manufacturing a nanovesicle including a heterodimeric G protein coupled receptor in accordance with one embodiment of the present invention.

Hereinafter, embodiments of the present invention will be described in details. However, the present invention is not limited to the embodiments.

<Embodiment 1> Manufacturing Nanovesicle Including Sweet Taste Substance Receptor Protein (hTAS1R2 and hTAS1R3)

<Embodiment 1-1> Manufacturing Taste Receptor hTAS1R2 and hTAS1R3

A cDNA of a heterodimeric G protein coupled receptor (heterodimeric GPCR) including the genes hTAS1R2 and hTAS1R3 having a HA-tag gene attached to a N terminal thereof was inserted into a pCMV6 vector. The resulting product as an original product was subjected to PCR amplification.

A single sequence of the PCR amplifications involves 94° C. 5 minutes, 55° C. 30 seconds, 72° C. 1 minute of the PCRs in this order using a Taq polymerase mixture (1.5 mM $MgCl_2$, 0.2 mM dNTPs, respective primers 0.5 mM, 100 ng plasmid). The sequence was repeated 35 times. The resulting PCR-amplified product was subjected to treatment using Kpn I and Xho I restriction enzymes. Then, the treated product was melt using a gel electrophoresis method to be separated.

The amplified heterodimeric receptor gene including the hTAS1R2 and hTAS1R3 containing therein the HA-tag was subcloned into the pCMV6 vector. The pCMV6 vector has DsRed genes at C terminal multi-cloning sites, and a target gene was expressed into a DsRed binding protein. Whether the cloning is carried out correctly was check using DNA sequencing.

<Embodiment 1-2> Manufacturing HEK-293 Cell Lines Stably Expressing hTAS1R2 and hTAS1R3

HEK-293 cell lines were transformed into the pCMV6 vector having the cloned hTAS1R2 and hTAS1R3 therein manufactured in the embodiment 1-1 using Lipofectamine 2000 (Invitrogen, USA). The HEK-293 cell lines transformed into the hTAS1R2 and hTAS1R3 so as to stably express the hTAS1R2 and hTAS1R3 were manufactured by a selective separation process using G-418.

After one day, the transformed cell lines were displaced into a culture medium including G-418 (1 mg/ml), and then were cultured therein for 14 days. Colonies having the expressed heterodimer including the hTAS1R2 and hTAS1R3 were generated. Then, only the generated colonies were selectively displaced into a culture medium including G-418 (0.5 mg/ml) using a DsRed fluorescence technique. The cells stabilized and cultured in the culture medium were subjected to Trypsine-EDTA (TE; Gibco, USA) treatment and, then, were re-floated using Dulbecco's phosphate buffered saline (DPBS; Gibco, USA), and, next, were subjected to sonication for 5 minutes (on time: 3 seconds, off time: 5 seconds) in a cooled atmosphere using ices. Along with the sonication, the resulting product was subjected to a centrifugal treatment at 12000 rpm, at 4° C., for 30 minutes. Thereafter, resulting pellets were finally re-floated at a 1000 ng $mL^{-1}$ concentration for further storage at −80° C.

<Embodiment 1-3> Manufacturing Nanovesicle Including hTAS1R2 and hTAS1R3

The cells transformed into the hTAS1R2 and hTAS1R3 and cultured in the embodiment 1-2 were subjected to a cytochalasin B (20 g/ml) treatment and then were incubated at a 300 rpm, at 37° C. for 20 minutes.

In order to perform separation between remaining cell bodies and nanovesicles, a centrifugal treatment was carried out at 1,000×g for 20 minutes. The obtained supernatant includes the nanovesicles. The supernatant including the nanovesicles was subjected to a centrifugal treatment at 15,000×g for 30 minutes, to obtain pellets. Then, a protease inhibitor cocktail (Sigma Aldrich, USA) was added using DPBS, such that the obtained pellets were re-floated. The resulting nanovesicles were directly used or were stored at −80° C. for several weeks later use.

The resulting nanovesicles were analyzed in a diameter thereof using a DLS (Dynamic Light Scattering) method. The analysis results are shown in FIG. 2E where it was confirmed that each of the diameters of the nanovesicles ranges between 100 nm and 250 nm, on average 150 nm.

<Example Experiment 1> Checking Recombinant Protein Expression

It was confirmed using a western blot method that a sweet taste substance receptor protein (hTAS1R2 and hTAS1R3) was expressed in the transformed cells.

The transformed cells were mixed with a sample buffer (10% sodium dodecyl sulfate, 10% β-mercaptanol, 0.3 M Tris-HCl (pH 6.8), 0.05% bromophenol blue, 50% glycerol) at 0° C. The mixture was incubated at 50° C. for 2 hours. The sample was loaded onto a 10% PAGE gel, and then was subjected to an electrophoresis treatment at a constant 80 V. The protein in the gel was indicated using a 0.02% coomassie-blue dying solution. The protein in the gel was displaced to a nitrocellulose membrane. The membrane was incubated in PBS-T (PBS with melted 0.1% Tween-20) with melted 5% skim milk for 2 hours for blocking. The blocked membrane was incubated together with an anti-GST antibody (anti-HA mouse antibody) (diluting the PBS-Tween with 1% skim milk at 1:2000) for one hour. Thereafter, the incubated product was cleaned using PBS-Tween five times, each time consuming 10 minutes. The membrane-treated antibody was incubated with a HRP-conjugated antibody (diluting the PBS-T with 5% skim milk at 1:2,500). Thereafter, the incubated product was cleaned using PBS-Tween five times, each time consuming 10 minutes. The western blots were expressed using an enhanced chemiluminescence detection kit (ECL: GE healthcare).

The western blot analysis result is shown in FIG. 2A, while microscope analysis result is shown in FIG. 2B. As shown in FIG. 2A and FIG. 2B, a size of the recombinant protein is detected at two bands 95 kDa and 180 kDa. Those two bands are proved to correspond to a size of a protein in a monomer form and a size of a protein in a dimer form respectively.

<Example Experiment 2> Checking Signal Transfer Via Transformed Cell and Nanovesicle A signal transfer via a sweet taste substance of each of the nanovesicle and HEK-293 cell was checked wherein the HEK-293 cell has the expressed heterodimeric receptor including the hTAS1R2 and hTAS1R3 manufactured in the embodiment 1, and the nanovesicle is separated from the HEK-293 cell.

For this, the transformed HEK-293 cell line was incubated for three or more days. Then, 5 μm Fura 2-AM (acetoxymethyl) (calcium indicator, Invitrogen) was loaded on the cells in an imaging buffer solution (NaCl 140 mM, KCl 5 mM, $MgCl_2$ 1 mM, $CaCl_2$) 2 mM, HEPES 10 mM, Glucose 10 mM, 0.1% Pluronic F-127, pH 7.4). A non-specific esterase residing in the cell performs hydrolysis for an AM ester group to be changed into a form sensitive to $Ca^{2+}$ ions. After incubation at 37° C. for 30 minutes, the cells were cleaned using the same buffer solution three times, and then were incubated at 37° C. for one hour such that the AM ester group was removed by the esterase in the cells.

After three times cleaning using respective solutions, a ligand and ATP (100 uM) for a $Ca^{2+}$ dependent fluorescence signal was injected thereto, and, dual stimulations (340 nm, and 380 nm) were applied thereto. Thereafter, a fluorescence signal due to $Ca^{2+}$ at 510 nm was measured using a spectrofluorophotometer. The fluorescence signal was obtained at 2 seconds intervals. A final result was shown as a ratio between fluorescence strengths resulting from the dual stimulations.

As shown in FIG. 2C, when 10 mM sucrose was added to the transformed HEK-293 cell line, it was confirmed that a fluorescence emission strength relatively increases. Further, as shown in FIG. 2F, when a 10 mM sucrose was added to the nanovesicle including TAS1R2 and TAS1R3 separated from the transformed HEK-293 cell line, it was confirmed that a fluorescence emission strength relatively increases.

<Embodiment 2> Manufacturing Field Effect Transistor Based Taste Sensor

Figure 3A:
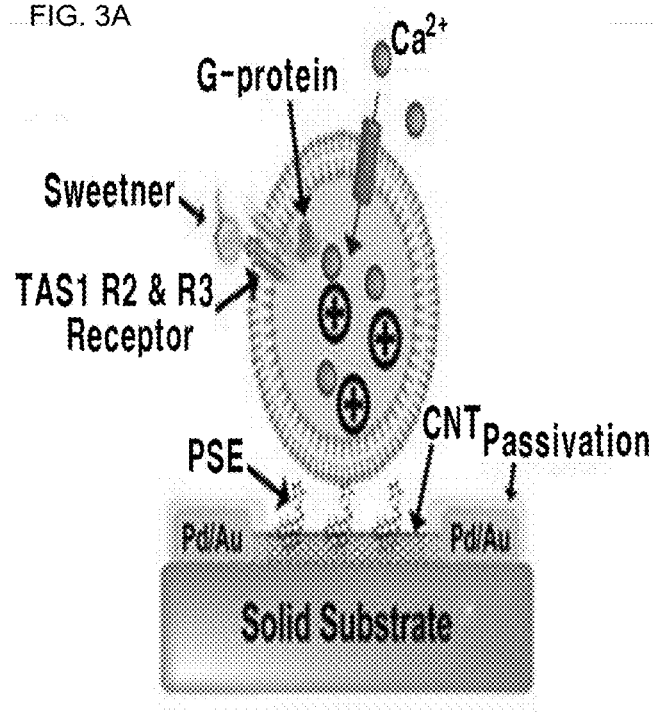
FIG. 3A schematically illustrates a taste detection mechanism of a field effect transistor based on a nanovesicle including a heterodimeric G protein coupled receptor, manufactured in accordance with one embodiment of the present invention.

A structure of a field effect transistor based taste sensor manufactured in accordance with the present invention is schematically shown in FIG. 3A.

A single wall carbon nanotube (swCNT) (2.5 mg, Hanwha (Korean Company)) was subjected to an ultrasonic vibration treatment for 20 minutes so as to be dispersed in 1,2-dichlorobenzene (50 ml). This resulted in a 0.05 mg/ml single wall carbon nanotube suspension. An octadecyltrichlorosilane (OTS) self-assembled monolayer (SAM) having a non-polar terminal group was patterned on a $SiO_2$ (1000 Å) substrate using a photolithography process. The patterned substrate was received in the single wall carbon nanotube suspension for about 10 seconds, and, then was cleaned using 1,2-dichlorobenzene. In this process, a single layer of the single wall carbon nanotube was selectively absorbed onto an exposed portion of the $SiO_2$ substrate where the OTS SAM was not formed.

A contact electrode was manufactured using a Pd/Au (10 nm/30 nm) evaporation and lift-off method. A gap size between source and drain electrodes was 20 mm. The electrodes were passivated with a photoresist (AZ 5214) using a photolithography process, the single wall carbon nanotube surface was modified with an amine group using PSE (pyrenebutyric acid succinimide ester). Then, the nanovesicles were immobilized onto the modified surface. In this connection, a pyrenyl group of the PSE (pyrenebutyric acid succinimide ester) reacts with a graphite in a side wall of the single wall carbon nanotube via 7E stacking. The nanovesicle including the sweet taste substance receptor in accordance with the present invention are immobilized via peptide binding onto the modified single wall carbon nanotube surface as the field effect transistor substrate surface.

The nanovesicles containing the sweet taste substance receptor protein (hTAS1R2 and hTAS1R3) collected in the embodiment 1 were spread evenly to cover the single wall carbon nanotube and the electrodes and then were subjected to a vacuum dry treatment for about 4 hours. The sweet taste substance receptor protein (hTAS1R2 and hTAS1R3)-containing nanovesicles were immobilized onto the single wall carbon nanotube, thereby to form the field effect transistor functionalized by a human sweet taste substance receptor.

<Example Experiment 3> Analyzing Characteristics of Field Effect Transistor

Figure 3B:
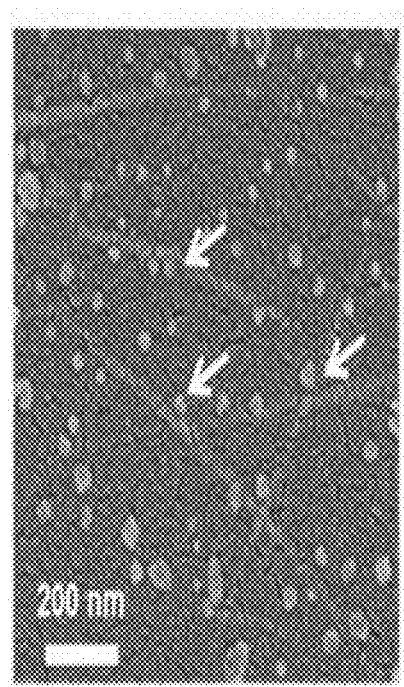
FIG. 3B shows a SEM (scanning electron microscopy) image of a nanovesicle immobilized onto a carbon nanotube in a field effect transistor based on a nanovesicle including a heterodimeric G protein coupled receptor, manufactured in accordance with one embodiment of the present invention.

A surface of the nanovesicle base field effect transistor manufactured in the embodiment 2 was subjected to a freeze drying using Pt. A FE SEM (field-emission scanning-electron microscopy) image of the surface is shown in FIG. 3B. It is confirmed as shown in FIG. 3B that a spherical nanovesicle is immobilized onto the single wall carbon nanotube, and a diameter of the immobilized nanovesicle is smaller than a diameter of the nanovesicle separated from the cell.

<Example Experiment 4> Signal Measurement for Taste Sensor

A sweet taste substance (Sigma Aldrich, USA) with a 1 mM concentration was dissolved into PBS (phosphate buffered saline; Gibco, USA) containing 2 mM $CaCl_2$) therein. The resulting solution was sequentially diluted ⅒ times to acquire a diluent.

The diluent was exposed to the nanovesicle based field effect transistor manufactured in the embodiment 2. A current between the source electrode and drain electrode was measured in a real time manner to check a reaction magnitude.

<Example Experiment 5> Sensitivity Measurement for Taste Sensor

A sensitivity $\Delta G/G_0$ of a sweet taste substance relative to sucrose in the nanovesicle based field effect transistor was measured in a real time manner. The measurement result is shown in FIG. 3C.

Figure 3C:
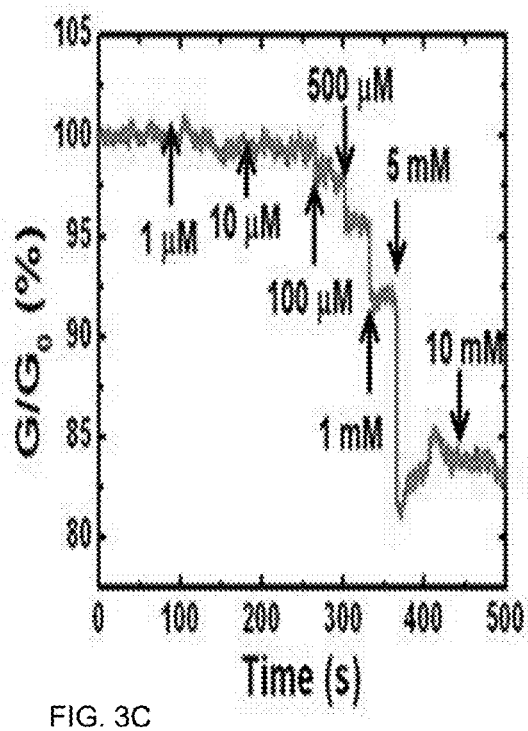
FIG. 3C shows a reaction result in a field effect transistor based on a nanovesicle including a heterodimeric G protein coupled receptor, manufactured in accordance with one embodiment of the present invention, wherein the reaction result is measured as a magnitude of a taste stimulus changes over time.
Figure 3D:
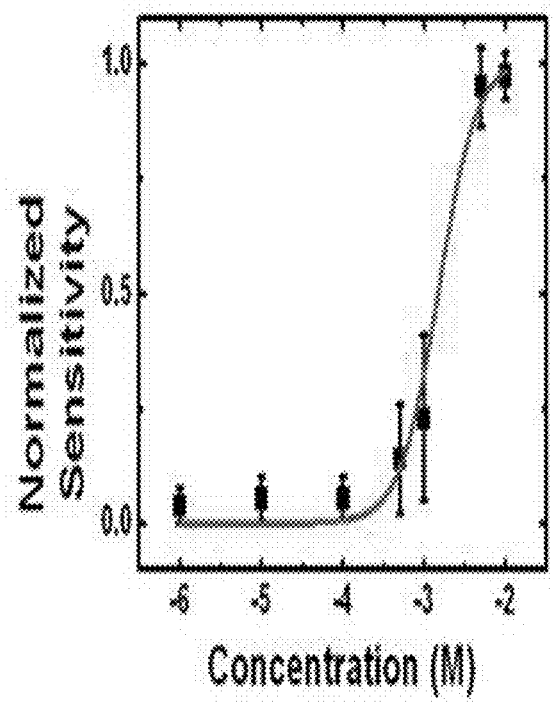
FIG. 3D shows a reaction over a concentration of a sweet taste stimulating substance for a field effect transistor based taste sensor manufactured in accordance with one embodiment of the present invention.

It is confirmed as shown in FIG. 3C that a signal generating from the taste sensor of the present invention decreases for a 100 uM sucrose concentration, and rapidly decreases for a 500 uM sucrose concentration. For various concentrations sucrose, a reaction curve of the nanovesicle based field effect transistor was applied to a hill equation as expressed below for a range of 100 uM to 10 mM. The application result is shown in FIG. 3D. In FIG. 3D, a solid line represents a previously known hill equation. Reactions over the concentrations in accordance with the embodiment of the present invention are represented as points in FIG. 3D.

$$C_s = C_{s,max} \cdot C^n / (1/K^n + C^n)$$

It is confirmed as shown in FIG. 3D that a reaction signal and stimulating substance concentration resulting from the taste sensor in accordance with the present invention meet the hill equation model.

When using the nanovesicle based field effect transistor, a taste substance may be detected at a concentration about 10 times lower than a detectable concentration by a cell based sweet taste substance detector. That is, the sensitivity may be improved.

<Example Experiment 6> Selectivity Measurement for Taste Sensor

In order to examine a selectivity of the field effect transistor based taste sensor of the present invention relative to the sweet taste substance, sucrose, aspartame, cellobios, fructose, saccharin, D-glucuronic acid substances were prepared, and were exposed to the field effect transistor based taste sensor manufactured in the embodiment 2.

It is shown in FIG. 4B that when 500 uM sucrose is added, a reaction magnitude decreases by about 5%; while when 100 mM cellobios, and D-glucuronic acid are added, there is no signal change. It is shown in FIG. 4C that when sweet taste sucrose and fructose, artificial sweet taste substance (saccharin and aspartame), taste-free sucrose are added, there is a signal change for the sweet taste sucrose and artificial sweet taste substance. In this connection, signals resulting from reactions of the nanovesicle based field effect transistor with the sweet taste sucrose and fructose, artificial sweet taste substance comply with the hill equation model.

Figure 1B:
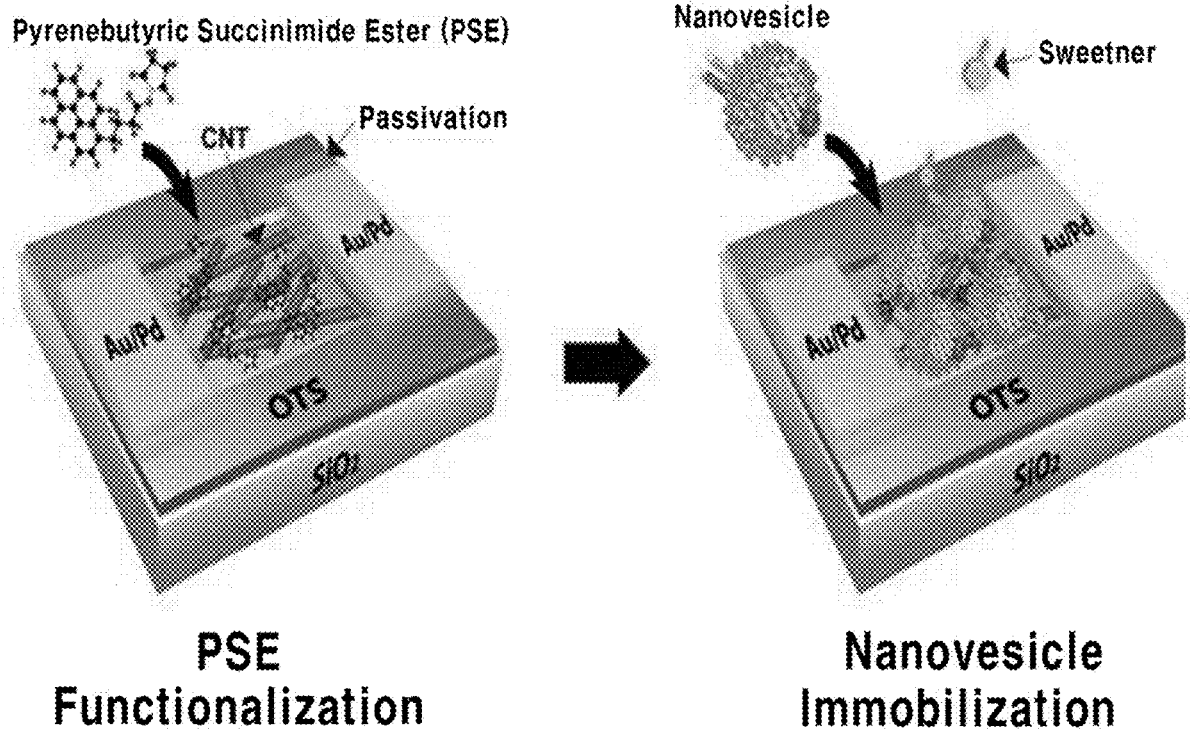
FIG. 1B shows a hybridization of the nanovesicles in accordance with one embodiment of the present invention with a sensor transducer based on a swCNT-FET.

To the contrary, when the taste-free sucrose is added, there is no signal change. Further, the artificial sweet taste substance including the saccharin and aspartame is more sensitive as a working substance than the sucrose. As shown in FIG. 4D, 1 mM concentration sucrose as contained in a coffee and Darjeeling tea usually available may be detected. The coffee and Darjeeling tea may be equally applied to the hill equation model as shown in FIG. 4C.

The above embodiments are merely examples listed for clear illustration, rather than limiting the implementations. Those of ordinary skill in the art can make other different forms of modifications or variations on the basis of the above illustration. There is no need to exhaustively list all the embodiments. Obvious modifications or variations derived therefrom are still within the protection scope of the present invention-creation. Although preferred embodiments of the present invention have been described above in detail in conjunction with the accompany drawings, the present invention is not limited to specific details in the above embodiments. Within the scope of the technical concept of the present invention, a variety of simple variations can be made to the technical solutions of the present invention, and these simple variations shall fall into the protection scope of the present invention. In addition, it should be noted that, various specific technical features described in the above specific embodiments can be combined in any proper manner without conflict. Further, a variety of different embodiments of the present invention can also be randomly combined, and as long as not departing from the thoughts of the present invention, the combinations should be deemed as contents disclosed by the present invention.

The field effect transistor based taste sensor functionalized by the nanovesicle including the heterodimeric G protein coupled receptor in accordance with the present invention may exhibit a similar reaction to as the human tongue feels a sweet taste. In this way, the effect transistor based taste sensor may be employed in a variety of fields including a medical, food, pharmaceutical, environment fields for sensing the taste substance.

What is claimed is:

1. A field effect transistor-based sweet taste sensor comprising:
   a substrate;
   source and drain electrodes formed on the substrate, wherein the source and drain electrodes are spaced from each other;
   a nanostructure formed on the substrate between the source and drain electrodes, wherein the nanostructure electrically contacts the source and drain electrodes; and
   a nanovesicle comprising an interior volume enclosed by a lipid bilayer and including a heterodimeric G protein coupled receptor at a surface of and/or within the lipid bilayer, the heterodimeric G protein coupled receptor comprising hTAS1R2 and/or hTAS1R3;
   wherein the nanovesicle is immobilized onto a surface of the nanostructure, wherein the field effect transistor-based sweet taste sensor is configured to measure a conductance variation resulting from positive ions flow into the interior volume of the nanovesicle via a cAMP pathway via binding between the heterodimeric G protein coupled receptor and a sweet taste substance.

2. The field effect transistor-based sweet taste sensor of claim 1, wherein the substrate surface comprises an amine group.

3. The field effect transistor-based sweet taste sensor of claim 1, wherein the nanostructure surface comprises at least one of the following selected from a group consisting of pyrene methylamine, 1-aminopyrene, and pyrenebutyric succinimide ester (PSE).

4. The field effect transistor-based sweet based taste sensor of claim 1, wherein the nanostructure includes a nanotube, nanowire, nanorod, nanoribbon, nanofilm, or nanoball.

5. A field effect transistor-based ligand sensor comprising:
   a substrate;
   source and drain electrodes formed on the substrate, wherein the source and drain electrodes are spaced from each other;
   a nanostructure formed on the substrate between the source and drain electrodes, wherein the nanostructure electrically contacts the source and drain electrodes; and
   a nanovesicle comprising an interior volume enclosed by a lipid bilayer and including a heterodimeric G protein coupled receptor at a surface of and/or within the lipid bilayer;
   wherein the nanovesicle is immobilized onto a surface of the nanostructure, wherein the field effect transistor-based ligand sensor is configured to measure a conductance variation resulting from a ligand contacting or interacting with the sensor.

6. The field effect transistor-based ligand sensor of claim 5, wherein the ligand is a ligand associated with taste.

7. The ligand associated with taste of claim 6, wherein the ligand associated with taste is a ligand associated with salty, sour, sweet, bitter, or savory taste.

8. The field effect transistor-based ligand sensor of claim 5, wherein the ligand is a saccharide, an amino acid, or an artificial sweetener.

9. The field effect transistor-based ligand sensor of claim 5, wherein the ligand is sucrose, fructose, glucose, maltose, lactose, D-tryptophan, aspartame, saccharin, acesulfame K, cyclamate, sucralose, cellobiose, or D-glucoronic acid.

10. The field effect transistor-based ligand sensor of claim 5, wherein the heterodimeric G protein coupled receptor comprises two genes selected from a group consisting of hTAS1R1, hTAS1R2, and hTAS1R3.

11. The field effect transistor-based ligand sensor of claim 5, wherein a conductance variation resulting from a ligand contacting or interacting with the sensor results from a signal system comprising a G protein, adenyl cyclase, and ion channels.

12. The field effect transistor-based ligand sensor of claim 5, wherein a conductance variation resulting from positive ions flow into the nanovesicle via a cyclic adenosine monophosphate (cAMP) pathway via binding between the heterodimeric G protein coupled receptor and a ligand.

13. The field effect transistor-based ligand sensor of claim 12, wherein the positive ions are calcium ions ($Ca^{2+}$).

14. The field effect transistor-based ligand sensor of claim 5, wherein the substrate surface comprises an amine group.

15. The field effect transistor-based ligand sensor of claim 5, wherein the ligand is contained in a solution or gas.

16. The field effect transistor-based ligand sensor of claim 5, wherein the nanostructure surface comprises at least one of the following selected from a group consisting of pyrene methylamine, 1-aminopyrene, and pyrenebutyric succinimide ester (PSE).

17. The field effect transistor-based ligand taste sensor of claim 5, wherein the nanostructure includes a nanotube, nanowire, nanorod, nanoribbon, nanofilm, or nanoball.

18. The field effect transistor-based sweet taste sensor of claim 1, wherein the nanovesicle has a diameter in the range of 100 nm to 250 nm.

19. The field effect transistor-based ligand taste sensor of claim 5, wherein the nanovesicle has a diameter in the range of 100 nm to 250 nm.

* * * * *